United States Patent [19]

Park

[11] 4,111,754
[45] Sep. 5, 1978

[54] IMMUNOLOGICAL TESTING DEVICES AND METHODS

[76] Inventor: Hydow Park, 2 Red Hill Rd., Warren, N.J. 07060

[21] Appl. No.: 745,541

[22] Filed: Nov. 29, 1976

[51] Int. Cl.² .......................... C12K 1/10; G01N 31/14
[52] U.S. Cl. .............................. 195/127; 195/103.5 A; 422/99; 422/68
[58] Field of Search ......... 195/127, 103.5 R, 103.5 A; 23/253 R; 424/12

[56] References Cited

U.S. PATENT DOCUMENTS

| 3,752,651 | 8/1973 | Bush | 23/253 R |
| 3,873,682 | 3/1975 | Ogawa | 424/12 |

Primary Examiner—Alvin E. Tanenholtz
Assistant Examiner—C. A. Fan

[57] ABSTRACT

A self-supporting plastic structure having a plurality of through-passages, each passage being of cross-sectional shape and area such that walls thereof provide a large amount of surface area relative to a substantially small amount of space cross-sectional area, each through passage having an upper funnel portion for receiving liquid, and a small outlet aperture of a smallness sufficient to effect a retention of liquid drop(s) within space of the through-passage by capillary action in the absence of additionally added fluid which by weight thereof forces liquid from the outlet aperture, and a separate washer structure seatable above the plastic structure and having a main liquid-containable vessel defined with a plurality of open outlets in the base thereof aligned for feeding contained liquid into separate ones of the through-passages simultaneously for the concurrent washing of each and all and/or for concurrent adding of further reagent or the like simultaneously concurrently to each and all.

11 Claims, 9 Drawing Figures

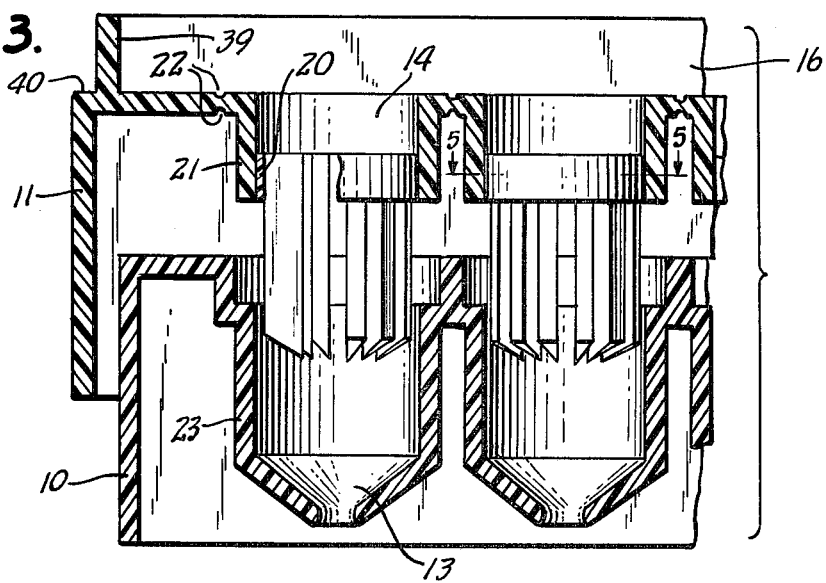
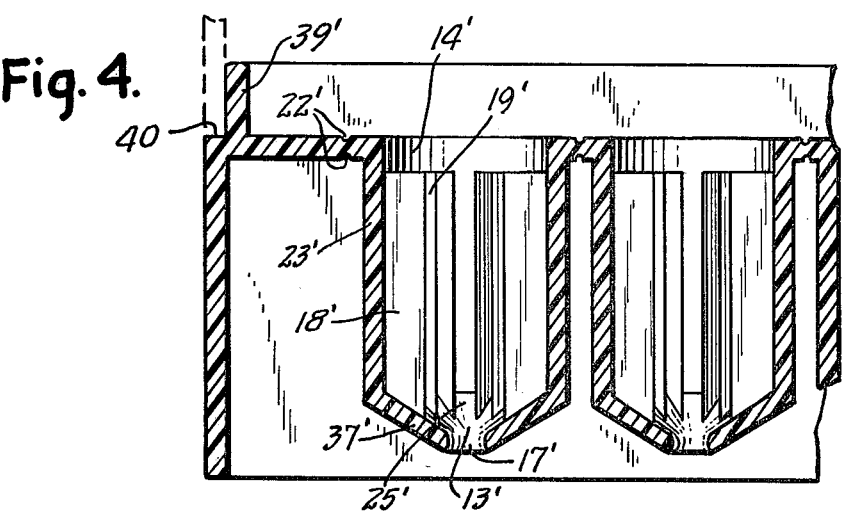
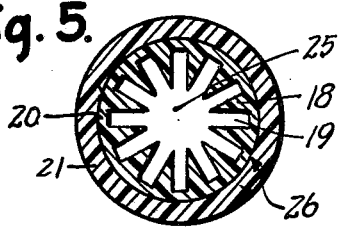
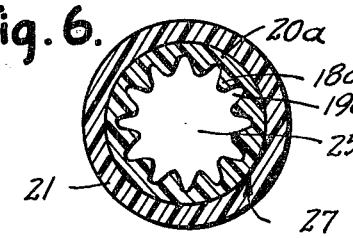
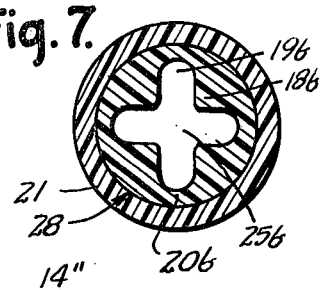
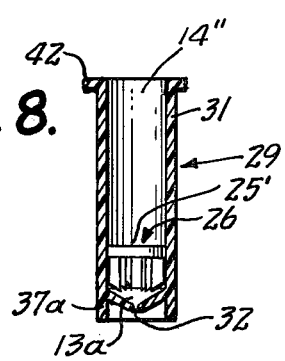
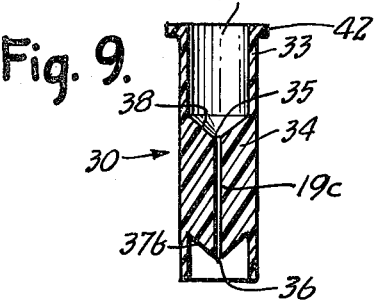

IMMUNOLOGICAL TESTING DEVICES AND METHODS

THE SPECIFICATION

This invention relates to novel and improved equipment and methods for immunological testing of typically antigens and antibodies.

BACKGROUND TO THE INVENTION

Prior to the present invention, typically for immunological testing there have been employed non-toxic disposable plastic plates of plastic such as polyvinyl or polystyrene, for example, to which attachment to the walls thereof by incubation is possible — as for example would occur upon addition of a fluid/liquid containing antigens to be counted and/or identified. After the incubation period, a tedious procedure of carefully washing each separately of a plurality of vessels per plate is required to both avoid contamination of one from another and to wash away all non-attached antigens, such procedure being attempted and accomplished by a variety of methods, all of which basically envolve the addition of washing water, then the withdrawal of the washing water. Such procedures are time-consuming and require special care and skill, and the results are less than highly accurate because of the difficulty in effecting clean washing even though several washings may be included within a procedure.

SUMMARY OF THE INVENTION

Accordingly, a primary object of the present invention is to obtain equipment and process(es) when are adaptable to a variety and multiplicity of immunological tests and procedures, while avoiding problems and difficulties of the type(s) described above.

Another object is to obtain a novel apparatus adaptable to speedy treatment and washings together with high efficiency and reliability in results obtained, for both single test procedures for a single specimen or antigen or the like, and for conducting consurrently and simultaneously a plurality of tests and/or specimens.

Another object is to obtain novel procedures utilizing such above-noted apparatus, achieving novel advantages together with avoiding disadvantages and difficulties of prior apparatuses and procedures.

Another object is to obtain increased relative linking-(attaching) of antigens and/or antibodies — as the case may be, to available wall surface area relative to total volume of the vehicle-liquid, during incubation, whereby less vehicle-liquid is required while intensity and/or positive-reading of the results is enhanced.

Another object is to obtain additional combination(s) of basic plate apparatus together with accessory washing apparatus coordinate in use and results, with the plate apparatus, for effecting reliable efficient and speeding testing of specimens of many different persons simultaneously and concurrently.

Another object is to obtain such plate apparatus, together with additional container-type plate apparatus of a throw-away nature.

Another object is to obtain a plate apparatus of the improved greater surface area relative to liquid volume-space, adaptable for detachably breaking-off one specimen-passage structure from other adjacent ones, such that radioisotope counter may be utilized in the ascertaining of the presence and concentration of radioisotopes and other such tracers.

Other objects become apparent from the preceding and following disclosure.

One and more objects are obtained by the invention of which various typical but not exclusive embodiments described hereinafter are merely typical, for purposes of understanding and illustration of the invention, and as to preferred embodiments thereof.

Broadly the invention may be described as a plastic structure typically of polyvinyl and/or polystyrene, or other plastic material to which, as conventionally known, one or more of antigen or antibody or other agent, specimen, or reagent required for a particular test, will adhere, attach and/or link, as the case may be; and the plastic plate-like structure must be self-supporting at least to an extent that when in its operative position for use, the base of through-passage upright and/or vertical passage structure's lower end is suspended above a supporting surface to thereby avoid contamination from the surface and to allow flow of water or other liquid to drain to the surface through the passage; and the cross-sectional area of space defined within the through-passage must be sufficiently small and the length of the through-passage along a length longitudinal axis thereof must be sufficiently elongated, such that wall surface area within the through-passage in the area or vicinity of the small cross-section, is large in ratio to the cross-sectional area of space at that same vicinity, i.e. where the surface area relative to volume, is large; and the through-passage has an upper structure which is basically liquid-receivable — i.e. a funnel structure in function, for receiving a particular liquid, avoiding the possibility of accidental overflow or spilling-over into an adjacent through-passage. It is to be understood, of course, that the support structure may be integral or not integral, and may be in fact another apparatus such as a conventional immunological testing plate having a plurality of wells of container spaces therein, on top of which the above-noted inventive appatatus may be seated with the through-passage structures possibly extending-downwardly into the well of container spaces, one per well of container space.

However, it is within the scope of the invention for there to be either a mere single through-passage per entire apparatus, or in an embodiment for use in handling large volumes of patients, and specimens thereof, a plurality of through-passages — and structures thereof, arranged in columns and rows. For the embodiments having a plurality of through-passage structures, of which the cross-sectional shapes thereof are preferably each of a dimension such that capillary action is retainable of liquid within the through-passage space thereof to obtain the high ratio of surface area to liquid volume at that vicinity within the through-passage, a washing structure having a plurality of outlets matchable with spaces, one per space, of the through-passages. In another preferred embodiment, there is provided either by integral structure or alternatively by a separate plate-like structure, a collector structure having a small aperture in it, although there could be multiple apertures, such collector structure being possitioned in close proximity with lower end(s) or portions of wall structures within each respective through-passage, whereby drop(s) of liquid within and/or hanging to lower end(s) or portion(s) of the inner wall structure of the through-passage is facilitated in being tentatively retained thereat; upon adding of additonal liquid and/or reagent, or the like, into the funnel structure of that particular through-passage space, weight of the added material forces liquid downwardly out of the through-passage space, as well as out-of the one or more small apertures of the collector structure. By virtue of such collector structure, the liquid vehicle — for example carrying the antigens initially, or at subsequent stages of treatment or testing steps, for retaining the antibody(ies) intermittently, improved attaching during incubation, and of linking, and the like are obtained, while nevertheless washing may be achieved by merely adding washing liquid (as water) to the funnel-structure portion of each of the through-passages; similarly, when adding reagent or the like, such excess merely passes downwardy and out of the collector structure small aperture(s), but is retained until washed through by subsequent addition of other material or upon subsequent washing.

In another combination, a washing apparatus includes a liquid container such as to obtain a large volume of water that may be poured easily thereinto, and the container structure has a plurality of bottom outlets preferably of funnel-like structure with the outlets aligned with and above the funnel portions of the respective ones of the plurality of through-passages, in order that simultaneously and concurrently the plurality may all be washed and/or a common liquid or reagent or the like added to all of the plurality of through-passages. The container structure may be separate from the structure of the through-passages, or alternatively may be seatable thereon for intermittent use therewith.

In another preferred embodiment, the passage (through-passage) structure may have scored lines or etched or compressed lines defining intermediate boreders between adjacent through-passage structures, thereby providing for easy breaking-off or shearing of one or more through-passage structures from other one or more through-passage structures, such as is required when a single treated structure is to be tested alone for the presence of radioactive isotopes or tracers or the like, in radioimmunoassay or the like.

THE FIGURES

FIG. 1 illustrates in top and side perspective view a preferred combination, shown in exploded view, of a plate-like collector structure having a plurality of collectors, over and into which fits the plastic through-passage structure having a plurality of separate through-passage structures extending downwardly into the respective ones of the collectors, and the liquid container and washing structure positioned and seated over the through-passage structure.

FIG. 3 illustrates a side-cross-sectional and exploded view of the combination of the collector structure and the through-passage structure, in an in-part view thereof.

FIG. 4 illustrates an alternate embodiment in side-cross-sectional and in-part view, of a unitary structure including both through-passage structure and collector structure.

FIG. 5 illustrates a cross-sectional view as taken along line 5—5 of FIG. 3.

FIGS. 6 and 7 illustrate alternative through-passage configurations as would be viewed in cross-sectional views such as that of FIG. 5.

FIGS. 8 and 9 illustrate in axial-longitudinal cross-sectional view single through-passage structure embodiments, as two typical alternate embodiments of that embodiment of the invention.

DETAILED DESCRIPTION

Figure 1:
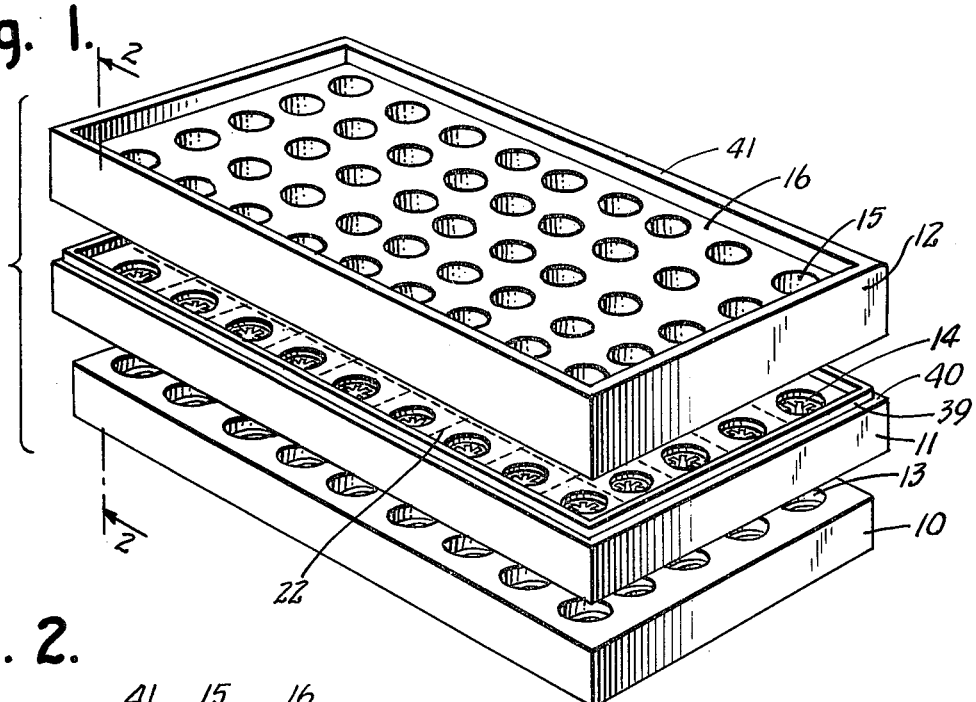
Figure 2:
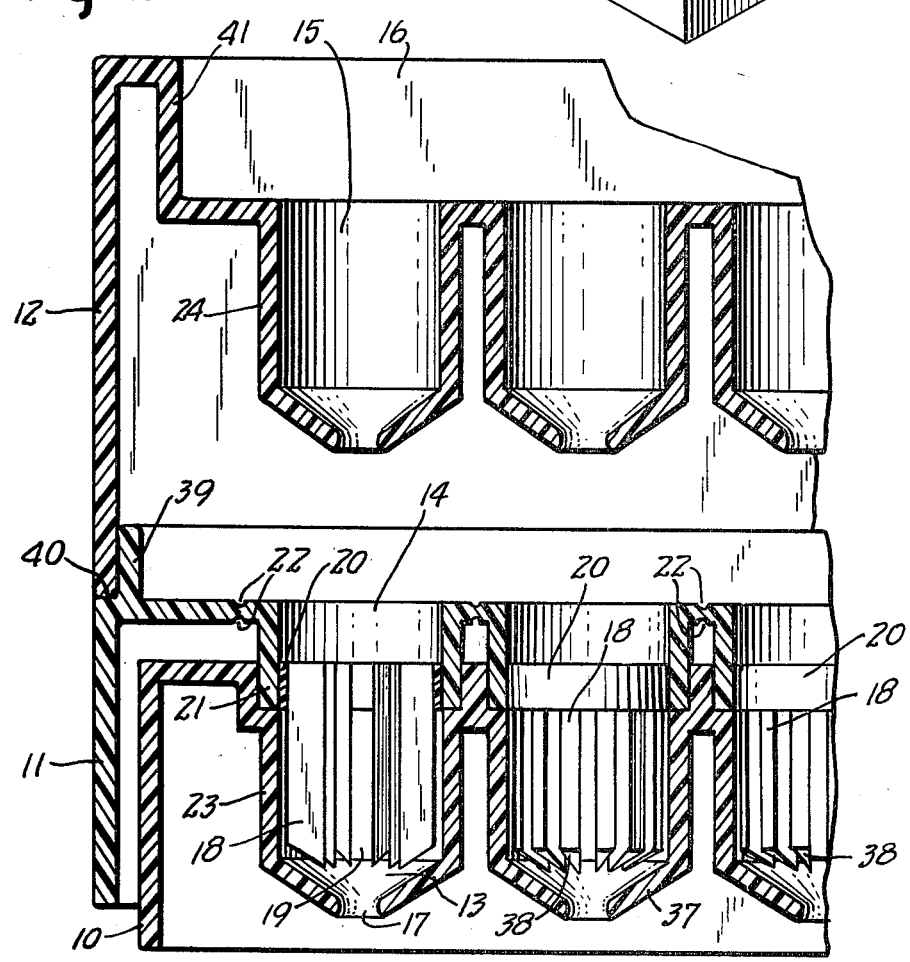
FIG. 2 illustrates a side-cross-sectional view in an in-part view of the FIG. 1 combination, in the seated states.

For purposes of description, reference is first made to the illustrations of FIGS. 1, 2, and 3, which disclose basically common elements.

In particular, there is the collector structure 10 as an overall unit, having seated thereover and thereon the plastic through-passage structure 11, and the washing structure (as a whole) 12. In the collector structure 10, there is collector space 13 in each separate collector 23 having lower small outlet 17. The plastic through-passage structure 11 has a plurality of through-spaces 14 in the funnel portion and 19 in the wall surface-coating portion. The irregularly-shaped wall-structure 18 (inner wall-structure of the through-passage) includes a unifying ring-portion 20 either wedged or fused in close-fit relationship with downwardly-extending tubular portion 21 separable from other adjacent downwardly-extending tubular portions by virtue of the score-line 22 seen in each of FIGS. 1 through 4. The downwardly-extending tubular portion 21 is viewable in transverse cross-section of FIGS. 5, 6, and 7, and unifying ring portions 20, 20a, and 20b, and through-passage inner-wall structures 18, 18a, and 18b, and liquid-retaining spaces 19, 19a, and 19b, and central bore spaces 25, 25a, and 25b being also viewable in these Figures, for the embodiments 26, 27, and 28 respectively. Each separate downwardly-extending funnel-like structure 24 of the washing structure 12 extends from a liquid container 41 having liquid containing space 16, with the outer supporting wall's base being seated as shown in FIGS. 1 and 2 snugly circumscribing ledge 39 and on seat (upper face) 40. The base bottom-face of inner-wall structure 18 preferably as face 38 angles radially inwardly and downwardly, as seen in FIGS. 2 and 3, and likewise the inner face of the collector-structure 23 downwardly extending follows the angularly downwardly and radially inwardly-extending structure 37, whereby liquid tends to flow in a radially inward or central direction into outlet aperture 17, the lower portion or faces 38 and other lower portions of the wall 18 never-the-less remaining in contact with such liquid and by capilliary action serving to retain liquid within spaces 19 and 25, and 13.

The alternate embodiment of FIG. 4 is a unitary structure comparable to the two separate apparatuses of FIG. 3, having inner walls 18' of the through-passage structure 23', with inner central space 25' and peripheral inner spaces 19' and collector space 13' adjacent outlet aperture 17', formed within tubular collector-structure such as typically the downwardly-extending conical wall 37'. The retainer-structure portion has a wall-retaining flange 39' around which a washing structure 12 (of FIG. 2) would seat onto seat 40', this embodiment also preferably having a score line 22', and recessed upper ends of walls 18' thus providing fill-space 14 preventing likelihood of overflow into adjacent through-passages.

FIGS. 8 and 9 illustrate embodiments each of which have a single through-passage and structure thereof, as through-passage structure 29 and through-passage structure 30. The through-passage structure 29 has typically the insert ring and wall (inner) structure embodiment 26 (of FIG. 5), and collector lower conical wall structure 37a with its aperture 32 of the overall through-passage structure having upper wall 31 and upper funnel-space 25, and collector space 13a.

The alternate embodiment 30 capitalizes principally on the fact of reduced wasted-space (in a sense), together with having a sufficiently small tubular space 19c as to effect capilliary action, and the small volume of liquid being more easily and completely depleted of, for example, antigens carried within liquid within that space because of the close proximity of all antigen bodies to wall surface(s) of the surrounding inner tubular walls of the passage tubular space 19c; as with other embodiments, the upper portion of the through-passage structure has the funnel-forming wall 33 forming funnel-space 25'' with the funnel (conical) wall structure 38 having inlet 35 to the tubular space 19c. As in the FIG. 8 embodiment, the embodiment 30 has outlet aperture 36 formed within the conical wall 37b.

The method of use of the present invention is novel as is the apparatus(es) of the invention, making possible the elimination of tedious and slow procedures. It should be noted firstly, that the through-passage structure 11 of any of FIGS. 1, 2, or 3, may be utilized alone as the sole inventive structure, while there are additional advantages to be obtained by the combination with the collector structure 10 and/or the washing structure 12. Accordingly, a precalculated and thus predetermined and measured amount of, for example, antigen-containing liquid may be introduced into funnel space 14 in an amount that will fill at-least a lower portion of the spaces 19, and 25, buw which normally will be insufficient in weight to normally (at least to any significant extent) flow-out through the lower end as drops or droplets, i.e. the antigen-containing liquid being held by capilliary action in the spaces in close proximity to the wall surface area onto which antigens attach to the plastic walls. It should be further noted that heretofore the walls to which the antigens attached were the container walls of a immunological plate, and other apparatuses such as diluters and/or washing apparatuses were not used for such function. In this invention, the flow-through apparatus is in fact the antigen-collector — i.e. the surface area to which antigens attach during incubation. After an incubation period, which because of the large surface area relative to the small volume of antigen-containing vehicle-liquid, obtains a highly efficient coating, a washing liquid is introduced in any needed quantity and as such is introduced, the weight thereof causes the same to move downwardly on top of the prior vehicle, causing the antigen-depleted vehicle-liquid to become forced-out of the lower spaces 19 and 25. Thereafter, a next reagent is added, such as adding serum in the same precalculated and measured amount — such forcing-out and replacing the heretofore-retained washing water; thereafter, an incubation period is allowed for attachment of antibodies to respective ones of the attached antigens. Thereafter, there is again introduced washing water, followed by introducing an enzyme-labeled immunoglobulins reagent which by its weight replaces the washing water, after which there is another incubation period, followed by another washing, followed by introducing a substrate reagent, followed by measuring absorption by spectrophotometer. It is to be understood that this is merely an illustrative example, and that instead of this entire procedure, a radioisotope or the like may be added as one step, followed by incubation, and by then washing, and then separating that particular through-passage downwardly-extending structure from adjacent ones and then testing for radio-activity thereof, for example.

The same procedure would be conducted when utilizing the combination of FIG. 3, with or without the preferred washing structure 12 of FIG. 2 during washing, and likewise the same procedure can be followed with the embodiments of FIG. 4, 6 and 7, as well as with the embodiments of FIGS. 8 and 9 respectively.

The utilization of the collector structure 10 or of the embodiments of FIG. 4 or FIG. 8 (embodiment 29) or FIG. 9 (embodiment 30), results in retaining a larger column-height of water and/or vehicule-liquid or reagent within the spaces 19, 25 and 13, or 19', 25', and 13' or 19c, for example — there being no separate collector as-such for embodiment 30.

The funnel spaces 14, 14', 14'' and 14''' serve as volumous spaces into which the liquid may be easily introduced in the precaulculated and measured amount, or during washing, without likelihood or overflowing the upper-wall edges thereof, thus avoiding contamination. In like manner, it will be noted that the apertures 17, 17', 32 and 36 are supported above the level of a supporting surface that would be located therebeneath during use. For use in a test-tube rack, the embodiments 29 and 30 have upper flanges, illustrated as a preferred embodiment feature thereof but optional, as flanges 42 and 42'.

When not utilizing the specific washer of this invention, conventional or otherwise-desirable washing apparatuses and procedures may be utilized.

The assay systems described above, and apparatus(es) and combinations thereof may be utilized for typically the following known general test methods, adapted as set forth above:

(a) Enzyme-linked immunosorbent assay, non-competitive, for the determination of antigens;
(b) Enzyme-linked immunosorbent assay, non-competitive, for the determination of antibodies;
(c) Enzyme-linked immunosorbent assay, competitive, for the determination of antigens;
(d) Radioimmunoassay, non-competitive, solid phase, for the determination of antigens;
(e) Radioimmunoassay, non-competitive, solid phase, for the determination of antibodies;
(f) Radioimmunoassay, competitive, solid phase, for the determination of antigens;
(g) Competitive protein binding radioassay, solid phase;
(h) Non-competitive protein binding radioassay, solid phase;
(i) Competitive protein binding enzymoassay, solid phase; and
(j) Non-competitive protein binding enzymoassay, solid phase; these not being exclusive nor limiting of the scope of the invention. The above-note procedures (a) throgh (j) would be typically conducted as follow:

Method (a):
1. Coat the walls (18 or 18', etc.) of the through-passage with specific antibodies;
2. Place a fixed volume of serum dilutions (or other specimens) and standards in each well(through-passage) of the assay system;
3. Incubate;
4. Wash; & dry;
5. Add a fixed volume of a solution of enzyme labelled antibodies to each well.
6. Incubate.
7. Wash; & dry;

8. Add a fixed volume of a chromogenic reagent to each well.
9. Read the result — as shall be noted below.

Method (b):
1. Coat the wells of an assay system with corresponding antigens;
2. Place a fixed volume of serum dilutions (or other specimens) and standards in each well of the assay system.
3. Incubate.
4. Wash; and dry;
5. Add a fixed volume of a solution of enzyme labelled anti-globulin antibodies to each well.
6. Incubate;
7. Wash and dry;
8. Add a fixed volume of a chromogenic reagent to each well;
9. Read the result.

Method (c):
1. Coat the wells of an assay system with a fixed amount of antibodies.
2. Place a fixed volume of serum dilutions (or other specimens) standards to each well of the assay system.
3. Add a fixed volume of a solution enzyme labelled antigens to each well.
4. Incubate.
5. Wash and dry;
6. Add a fixed volume of chromogenic reagent to each well.
7. Read the result.

Method D:
1. Coat the wells of an assay system with specific antibodies;
2. Place a fixed volume of serum dilutions (or other specimens) and standards into each well of the assay system.
3. Incubate.
4. Wash and dry.
5. Add a fixed volume of a solution of radio-labelled antibodies to each well.
6. Incubate.
7. Wash.
8. Count the radioactivity of each well.

Method E:
1. Coat the wells of an assay system with corresponding antigens;
2. Place a fixed volume of serum dilutions (or other specimens) and standards into each well of the assay system;
3. Incubate;
4. Wash and dry;
5. Add a fixed volume of a solution of radiolabelled anti-globulin antibodies to each well;
6. Incubate;
7. Wash;
8. Count the radioactivity of each well.

Method F:
1. Coat the wells of an assay system with a fixed amount of specific antibodies;
2. Place a fixed volume of diluted serum (or other specimens) and standards into each well of the assay system;
3. Add a fixed volume of a solution of radio-labelled antigens to each well;
4. Incubate;
5. Wash;
6. Count the radioactivity of each well.

Method G:
Follow the same procedure as for Method F, except:
(1) Use binding protein instead of antibodies; and
(2) the substance to be measured does not function as an antigen. Method H: The procedure is the same as that of Method D, except for the differences noted in method G-above. Method I: Competitive protein . . . method, the procedure is the same as that for Method C-above, with the exceptions of Method G; Method J: The procedure is the same as an enzymoassay of Method A-above, with the exceptions of the Method G.

In the use of the apparatus(es) of the invention, the entire stacked combination of FIG. 1 may advantageously be utilized as follow. If the same material is to be added to all wells (through-passages) during the first step, and similarly whenever for any subsequent step the same material is to be added to all wells, then it may be poured collectively into the space 16 in order to avoid having to individually place the same into each separately which would require considerable time. On the other hand, if after adding the different initial material to different ones of the wells, the same (common) material(s) and/or treatments are followed for all, the initial different materials may be added to the funnel space 14 of FIG. 3 combination or to the funnel space 14' of the FIG. 4 combination, and thereafter the apparatus of the washing structure 12 may be added (to obtain the FIG. 1 combination) for subsequent procedures in which the treatments of all wells are the same, and/or until the procedure differs again.

In order to effectively read the test results of enzymoassays for the present invention and apparatus thereof, any of the following procedures may be followed alternatively:
1. The color of the solution is assayed by a spectrophotometer after the enzyme activity is stopped; or
2. The color of the solution is inspected by eyes after the enzyme activity is stopped; or
3. The solution is drained into a white absorbent paper containing a chemical reagent that stops the enzyme activity, and the resulting color is inspected by ones eyes.

Draining may be effected advantageously by touching the absorbent paper surface to the aperture 17 or 17' or 32 or 36.

While the breadth of transverse cross-sectional measurements of spaces 19 have not been specified, it is advantageous that such be small enough in nature as to effect capilliary action, but such small dimension is not essential except in the embodiment 30, the large surface area relative to liquid volume being an advantage in any event.

For the various embodiments of FIGS. 1 through 4 and 7 and 8, the well-space (funnel-space) 14, 14', 14", and 14''', have a transverse (horizontal) cross-sectional width or diameter of typically from 0.5 to 3.0 cm., preferably from about 0.5 cm. to 2.0 cm.; with an upper well-depth (of these spaces 14, . . . ) of from about 0.2 cm. to 5.0 cm., preferably from about 0.3 cm. to about 2.0 cm.; and the diameter across space 19 & 25 ranges from about 0.3 cm. to about 2.0 cm., preferably from about 0.5 cm. to about 1.0 cm., at a depth (length of walls 18) from about 0.3 cm. to about 3.0 cm., preferably 0.5 cm. to aobut 1.0 cm.; and apertures 17, 17', 32 and 36 each range from about 0.05 cm. to about 0.5 cm., preferably from about 0.1 cm. to about 0.3 cm. The dimensions of 19' and 19a and 19b correspond to 19; and of 25a and 25b, etc., to 25; and of 19c to 36.

Aside from advantages already pointed out above, and aside from already stated objects, it might be noted that particualar advantages include:
1. Smaller volume of test material, reagents (enzyme and antisera) and the like, are required.
2. More effective coating is obtained.
3. Incubation is obtained in a shorter period of time.
4. The tests conventionally known, become more sensitive by use of the inventive apparatus(es) and procedure(s).
5. Easier and more effective washing are obtained.
6. The plates may be "pre-loaded" (pre-treated) with reagents, merely requiring the subsequent-adding of the final material(s) and washings where required.

it is to be understood that the invention is not limited to the specific embodiment illustrated, but include other embodiments within the scope of the appended claims, together with modifications, substitution of equivalents, and the like, to the extent that such would be obvious to a person of ordinary skill.

I claim:

1. An immunological testing device comprising: a plastic structure having upper and lower open ends, having a through-passage of predetermined small cross-sectional area sufficiently small to retain liquid by capillary action within space thereof at at-least substantially an intermediate portion of a length thereof, and the plastic structure being elongated along a longitudinal axis of the through-passage, the ratio of the wall surface area of said through-passage being larger than the cross-sectional area of said intermediate portion, and in which said plastic structure has formed therein an enlarged funnel structure in continuous flow-relationship with the upper end of the intermediate portion of the through-passage of said predetermined small cross-sectional area.

2. An immunological testing device of claim 1, in which said plastic structure has only a single through-passage.

3. An immunological testing device of claim 1, in which said plastic structure includes a plurality of said through-passages arranged in substantially parallel-flow relationship; and tubular collector-structure forming a common collecting space at lower-end outlets of said plurality.

4. An immunological testing device of claim 1, including a washing structure having a liquid containing structure with a plurality of spaced-apart funnel-outlets, and in which said plastic structure includes a plurality of said through-passages and of said enlarged funnel structures, and washing structure being seatable onto an upper portion of said enlarged funnel structures with each one respectively of the enlarged funnel structures positioned for receiving liquid flow from at least one of said spaced-apart funnel-outlets, the spaced-apart funnel-outlets thereby feeding washing liquid to separate ones of said enlarged funnel structures whereby through-passages associated with respective ones of each enlarged funnel structure are concurrently washable so as to be devoid of contamination between separate ones of the enlarged funnel structures.

5. An immunological testing device of claim 1, in which said plastic structure includes a plurality of said through-passages arranged in substantially parallel-flow relationship and in which through-flow spaces of said plurality of said through-passages are in flow-communication with one-another; and including a washing structure having a liquid containing structure with a plurality of spaced-apart funnel-outlets, said washing structure being seatable onto an upper portion of structure of a plurality of said enlarged funnel structure with each one respectively of the enlarged funnel structures positioned for receiving liquid flow from at least one of said spaced-apart funnel-outlets, the spaced-apart funnel-outlets thereby feeding washing liquid to separate ones of said enlarged funnel structures whereby through-passages associated with respective ones of each enlarged funnel structure are concurrently washable so as to be devoid of contamination between separate ones of the enlarged funnel structures.

6. An immunological testing device of claim 1 including a plurality of said enlarged funnel structure and pluralities of said through-passages, through-passages of different enlarged funnel structures being in segregated non-flow relationship to one-another.

7. An immunological testing device of claim 5, including means for detaching individual sets of an enlarged funnel structure and associated plurality of through-passages thereof, from other ones of enlarged funnel structures and associated through-passages thereof.

8. An immunological testing device of claim 7, in which said means for detaching comprises scored structure adapted for ease of severing structures from one-another.

9. An immunological testing device of claim 3, in which said tubular collector structure has a lower outlet aperture of predetermined small dimensional cross-section sufficiently small to effect retaining a drop of liquid within said common collecting space when devoid of liquid weight of additional liquid above said intermediate portion within said enlarged funnel structure.

10. An immological testing device of claim 3, in which spaces of the plurality of said through-passages are in common communication along longitudinal lengths thereof within a space formed centrally therebetween and interconnecting the through-passages of the plurality of said through-passages.

11. An immunological testing device of claim 10, in which said tubular collector structure has a lower outlet aperture of predetermined small dimensional cross-section sufficiently small to effect retaining a drop of liquid within said common collecting space when devoid of liquid weight of additional liquid above said intermediate portion within said enlarged funnel structure.

* * * * *